United States Patent [19]

Mora

[11] Patent Number: 4,644,087
[45] Date of Patent: Feb. 17, 1987

[54] DERIVATIVE OF (−)-6,6-DIMETHYLBICYCLO [3.1.1.]EPT-2-ENE-2-ETHANOL HAVING MUCOSECRETOLYTIC ACTIVITY, A PROCESS FOR ITS PREPARATION AND PHARMACEUTICAL COMPOSITIONS CONTAINING THE SAME

[75] Inventor: Camillo C. Mora, Piacenza, Italy

[73] Assignee: Camillo Corvi S.p.A., Italy

[21] Appl. No.: 742,575

[22] Filed: Jun. 7, 1985

[30] Foreign Application Priority Data

Aug. 8, 1984 [IT] Italy ............................ 22259 A/84

[51] Int. Cl.$^4$ .................................................. C07C 35/18
[52] U.S. Cl. ................................... 568/823; 568/824; 568/715
[58] Field of Search .................. 568/824, 823, 715

[56] References Cited

U.S. PATENT DOCUMENTS 2,815,378  12/1957  Klein ........................... 568/823

FOREIGN PATENT DOCUMENTS 764323  8/1971  Belgium ........................ 568/823

OTHER PUBLICATIONS

P. Ventura, M. Schiavi and S. Serafini, "The Metabolism of Trans-Sobrerol in the Rat", Xenobiotica, 1983, vol. 13, No. 3, 139–146.

Ventura et al, "Chemical Abstracts", vol. 99, (1983) p. 115465s.

Bain, "J. Amer. Chem. Soc.", vol. 68, pp. 638–642, (1946).

*Primary Examiner*—Warren B. Lone
*Attorney, Agent, or Firm*—Ostrolenk, Faber, Gerb & Soffen

[57] ABSTRACT

A novel derivative of (−)-6,6-dimethylbicyclo [3.1.1]ept-2-ene-2-ethanol (J. P. Bain, J. Am. Chem. Soc. 1946, vol. 68, page 638) is disclosed. The parent composition is marketed e.g. under the name nopol, v. The Aldrich-Europe Catalog Handbook of Fine Chemicals, item 3160-5 nopol 98% 128-50-7.

The object of the present invention is the compound of formula (I): 4-(2-hydroxyethyl) -ααdimethyl-5-hydroxy-3-cyclohexene-1-methanol, with the process for obtaining the same, which consists of the preparation of (−)-(6,6-dimethylbicyclo[3.1.1]ept-2-ene-2-ethanol epoxide, followed by hydration of the above compound. Finally, this invention comprises the pharmaceutical compositions containing the compound of formula (I) which have a mucosecretolytic pharmacological activity.

3 Claims, No Drawings

DERIVATIVE OF (−)-6,6-DIMETHYLBICYCLO [3.1.1.]EPT-2-ENE-2-ETHANOL HAVING MUCOSECRETOLYTIC ACTIVITY, A PROCESS FOR ITS PREPARATION AND PHARMACEUTICAL COMPOSITIONS CONTAINING THE SAME

DESCRIPTION

The object of this invention is the compound having the following structural formula:

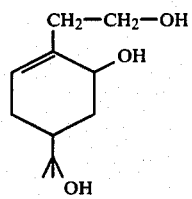

Code CO/1408, $C_{11}H_{20}O_3$, mol.wt. 200.28, m.p. 103°–105° C., 4-(2-hydroxyethyl)-α,α-dimethyl-5-hydroxy-3-cyclohexene-1-methanol. Unexpectedly, it has been found that (−)-6,6-dimethylbicyclo[3.1.1.]ept-2-ene-2-ethanol (also known as nopol) can be oxidized directly by conventional methods, that is without previously protecting the OH group by acetylation. While nopol is well known from scientific literature (see: "J. P. Bain, J. Am. Chem. Soc. 1946, Vol. 68, page 638") and it is commercially available (see, for example, The Aldrich-Europe Catalog Handbook of Fine Chemicals, n. 3160-5 Nopol 98% 128-50-7), no description has been known for the corresponding epoxide derivative of (−)-6,6-dimethylbicyclo[3.1.1]ept-2-ene-2-ethanol, the analytical characterization of which is reported in the present description.

For the epoxidation, peracids may be employed, such as perbenzoic acid, meta-chloroperbenzoic acid and particularly peracetic acid in a 40% acetic solution, in an anhydrous methylene chloride (ethanol free) medium, by using, as an acid acceptor, sodium carbonate in suspension. Concurrently with the epoxidation in the reaction medium, kept at from 5° to 10° C., there forms an equimolecular salt mixture of anhydrous sodium bicarbonate and sodium acetate, which at the reaction end, are eliminated by filtration of the chloromethylene solution of the epoxide; or, after water dissolution, the chloromethylene phase is separated, washed with water and dried. In both cases, by evaporating under reduced pressure, the methylene chloride is at last eliminated to obtain the concentrated epoxide (96%). After obtaining the epoxide of (−)-6,6-dimethylbicyclo[3.1.1]ept-2ene-2-ethanol of formula (II), this has led to make an investigation on the process of epoxide hydration, which may be obtained in an aqueous medium in the presence of diluted strong acids (1% solution of $H_2SO_4$, $H_3PO_4$) or, preferably, of weak acids (such as $H_2CO_3$ or $H_2SO_3$) at a temperature of 1° to 20° C. From the hydration products, the product of formula (I) which is an object of this invention can be separated at a good yield. The product of formula (I) of the present invention shows a very interesting pharmacologic activity as a mucolytic agent for bronchial secretion, and therefore the product of formula (I) is such as to potentially constitute a novel drug, soluble in water, which may be intended for the therapy of acute and chronic bronchitis as well as of bronchopneumonic diseases in general, associated with complications caused by thickening of the expectoration.

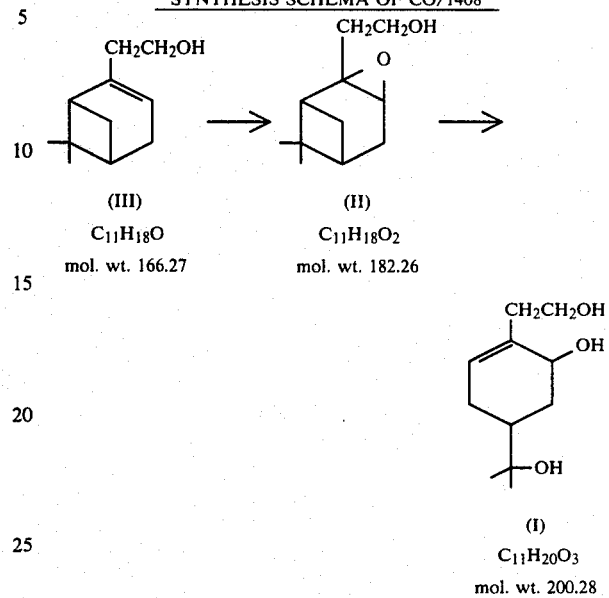

EXAMPLE

To a solution of 33.25 g of (−)-6,6-dimethylbicyclo[3.1.1.]ept-2-ene-2-ethanol in 200 ml of anhydrous methylene chloride, free from ethanol, 34 g of anhydrous sodium carbonate are added. The resulting mixture is cooled to a temperature of 5° to 10° C. and 60 ml of 40% peracetic acid, under vigorous stirring, are added thereto. At the end of the addition, the cooling is interrupted and the mixture is left under stirring at room temperature for 12 hours.

After dilution with water in order to dissolve the precipitated salts, the organic chloromethylene phase is separated, washed again with water, and dessiccated. Finally, the organic phase is evaporated under reduced pressure to eliminate the methylene chloride. 35 l g (96%) of concentrate epoxide are so obtained. To the above compound, 60 ml of water and 10 g of solid carbon dioxide are added, and the resulting mixture is vigorously stirred for 3 hours. It is diluted with water saturated with sodium chloride and extracted repeatedly with ethyl acetate. The combined organic phases are washed with a little water, are dried and concentrated to a volume of about 100 ml. The precipitate is filtered off (with suction pressure), to give 16.5 g (41%) of a product having m.p. 103°–105° C.

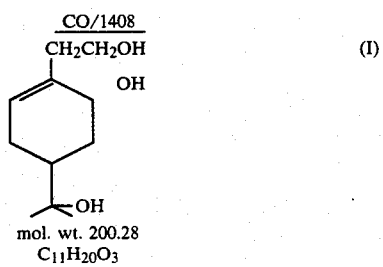

I.R. (nujol dispersion, cm$^{-1}$):
3280 νOH (broad band)

1160, 1038, 1021, 928, 827 characteristic bands
N.M.R. (solvent: $CD_3OD$; TMS reference; $\delta$ppm
- 5.67 centre, c.a. (1H; =CH)
- 4.07 centre, c.a. (1H; C$\underline{H}$—OH; $W\frac{1}{2}$=7,5 Hz)
- 3.65, c.a. (2H; $\underline{CH_2}$—$\overline{OH}$)
- 2.47÷1.07, c.$\overline{a}$. (7H; =$CH_2$—$CH_2$ and $\underline{CH_2}$—CH—$CH_2$)
- 1.19, s. (6H; gem $CH_3$)

c.a. = complex absorption  $W\frac{1}{2}$ = broadness at half height
s. = singlet
TMS = tetramethylsilane Elemental analysis

| Calculated | | |
|---|---|---|
| C = 65.97% | H = 10.07% | O = 23.96% |
| Found | | |
| C = 65.83% | H = 10.22% | |
| = 65.87% | = 10.18% | |
| = 65.78% | = 10.30% | |

MS (quadrupole; electronic impact; direct insertion; 75 and V; 0.80 mA; m/z):
200 (M+; 0.17%); 182[(M-18)+, 2.97%]; 167[M-18-15)+, 3.91%]; 164[(M-18-18)+, 1.42%]; 151(15.54%); 149(5.43%); 139 (10.13%); 138(4.05%); 137(3.75%); 133(2%); 126(3.62%); 123(5.60%); 122(3.65%); 121(27.83%); 111(7.22%); 109(7.80%); 107(6.23%); 105(6.74%); 95(17.91%); 93(19.15%); 91(27.09%); 81(16.01%); 79(20.49%); 78(18.85%); 77(14.80%); 67(19.84%); 59 (base peak).

Analytical data of the intermediate epoxide of (−)-6,6-dimethylbicyclo[3.1.1]-ept-2-ene-2-ethanol (II)

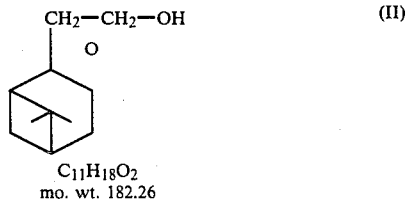

$C_{11}H_{18}O_2$
mo. wt. 182.26

I.R. (liquid film; $cm^{-1}$):
- 3240$\nu$ OH (broad band)
- 1387, 1370 gem-dimethyl
- 1270$\nu$ symmetric epoxide ring
- 1045$\nu$ C—O C—OH
- 868$\nu$ asymmetric epoxide ring N.M.R. (Solvent $CDCl_3$; TMS reference; $\delta$ppm): 3.65 t broadened (upon addition of $D_2O$, it narrows) (2H; —$CH_2$—OH; $\tau$=6.H2)
- 3.28 center c.a. (1H; >CH—O)
- 2.25÷1.45 c.a. (8H; CH—$CH_2$—CH—$CH_2$ and $CH_2$—$CH_2$—OH)
- 1.31 and $\overline{0.94}$ 2s (6H; gem. $CH_3$)

c.a. = complex absorption
t = triplet, TMS = tetramethylsilane
2s = singlets

M.S. (quadrupole, electronic impact; direct insertion; 70 eV; 0.80 MA; m/z):
182 (M+; 0.1%); 167 (M-15)+; 25%; 151(15%); 149(12); 146(5); 139(10); 137(15); 131(5); 126(10); 123(7); 121(16); 113(12); 112(12); 109(20); 107(14); 105(15); 95 (base peak); 93(30); 91(26); 83(34); 82(40); 81 (39); 79(43); 77(23); 73(36); 69(50); 67(91); 55(66).

TOXICITY

Method for studying the lethal dose 50 ($LD_{50}$) in the mouse after a single administration.

Groups of 10 Swiss albine, female, adult mice (20÷22 g of body weight), fasting from the evening preceding the test, are treated orally with varying doses of the test drug, suspended in hydroxyethylcellulose (0.5% w/v). Thereafter, the animals are fed again.

$LD_{50}$ is calculated with the method of J. T. Litchfield and F. wilcoxon (J. Pharmacol. 96, 99–113, 1949) by utilizing the mortality data as obtained on the 14th day after the administration of the test drug. The CO/1408 is tested at 1000-2000-4000 mg/kg/os in the mouse. No mortality or toxic behavioral symptomatology is found up to the maximum dose.

BRONCHOSECRETAGOGUE ACTIVITY

Method of quantitative evaluation of the rabbit bronchial secretion according to R. Scuri et al. Boll. Chim. Farm. 119, 181-7; 1980.

Adult male brown rabbits (2.8–3.5 kg of body weight) to which a T shaped tracheal cannula is applied by surgical operation, as described in the above cited bibliographic reference, are used.

To the cannula, a container for periodical collection of the bronchial secretion is applied.

The study of mucoproduction, started on the fourth day after the operation, is divided into two periods (of 4 hours each) for collecting and measuring the secreted mucus. The action of the test drug is proven by administering it orally at the beginning of the second period of mucus collection and evaluating the percent increase in the mucus production (as measured gravimetrically) in the second period in comparison with the first period.

Table No. 1 Bronchosecretagogue activity of CO/1408

Below are reported the average values of the percent increase of the bronchial mucus secretion upon treatment with CO/1408 and other known standards as compared to the basal values. Further, there is reported the number of rabbits which showed an increase of bronchial secretion as compared with all the animals treated with CO/1408 at the varying doses and via the two administration routes (R. Scuri et al, Boll. Chem. Farm., 119, 181-7, 1980).

| Dose mg/kg | Administration way | Bronchial secretion average increase, % | N° of rabbits with a secretion increase/ N° of rabbits CO/1408 treated |
|---|---|---|---|
| CO/1408 | | | |
| 25 | oral | 12 | 2/10 |
| 50 | oral | 53 | 6/10 |
| 100 | oral | 82 | 11/11 |
| N—acetylcysteine | | | |
| 400 | oral | 22 | 8/16 |
| 600 | oral | 59.4 | 6/9 |
| Bromhexine | | | |
| 200 | oral | 35.8 | 4/8 |
| 400 | oral | 43 | 6/8 |
| Carboxymethyl-cysteine | | | |
| 200 | oral | 10 | 4/10 |
| 400 | oral | 46 | 5/10 |

MUCOLYTIC ACTIVITY "IN VITRO"

Method for studying the viscosity of gastric mucin, in vitro, according to R. Scuri et al. Il Farmaco, Ed. Pr.-36, 36–48, 1981.

The test drug is kept in contact with a 5% water suspension of swine gastric mucin during 30 minutes (0.1 ml of the drug solution or 0.1 ml of solvent of the drug itself for the controls, in 1 ml of mucin suspension).

After incubation, the viscosity of each sample is measured by a Contraves microviscometer (RM model-cone and plate system, thermostat at 37° C.)

Table No. 2-Mucolytic activity "in vitro" of CO/1408

Below are reported the values of the viscosity decrease of the mucin caused by CO/1408 and other standards, calculated as average value of the decreases as measured at the 11 rotation speeds of the viscometer cone.

| Drug concentration, % | Average value of the viscosity decrease, % |
|---|---|
| CO/1408 | |
| 2 | 15.5 |
| 10 | 17.4 |
| Acetylcysteine | |
| 2 | 10.3 |
| 10 | 18.0 |
| Bromhexine | |
| 2 | 8.4 |
| Thiopronine | |
| 2 | 13.6 |

Referring to the activity shown by the compound of formula (I) as a mucosecretolytic agent, the present invention further provides pharmaceutical compositions which contain the compound of formula (I) in dosage unit. The pharmaceutical forms containing the above mentioned active ingredient are those for intramuscular and intravenous administration, and those for aerosol, as well as the ones for oral administration: in particular capsules, tablets, granular forms in sachets, syrups and forms for rectal administration (suppositories).

In the forms as mentioned, conventional excipients are combined with the compound of formula (I).

In the solid oral forms (tablets, capsules, granular forms) the preferred excipients are: lactose, starch, cellulose and its derivatives, with all the carrier materials for the preparation of the given pharmaceutical form, such as precipitated silica, talc, calcium or magnesium stearate.

In the form of syrup, the active compound is dissolved in a sugar solution (saccharose, glucose, sorbitol) with addition of aromatizing and preserving agents.

In the form of suppository, the main excipient consists of fatty acid triglycerides, either pure or as a mixture with oxyethylated derivatives.

In the injectable or aerosol forms, compound (I) is brought to an isotonic solution and cold or hot sterilized.

I claim:

1. 4-(2-hydroxyethyl)-α,α-dimethyl-5-hydroxy-3-cyclohexene-1-methanol of the formula:

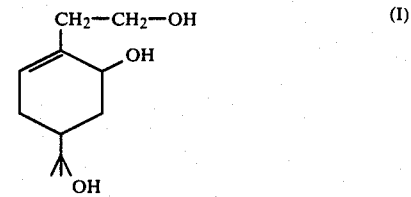

2. Pharmaceutical composition having mucosecretolytic activity, comprising an effective mucobroncosecretolytic amount of

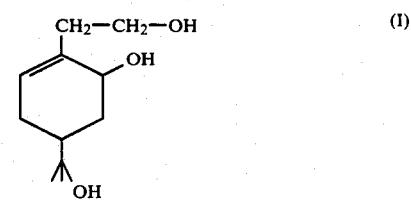

and a pharmaceutically acceptable carrier.

3. A method of increasing mucosecretolytic activity which comprises administering to a host an mucobroncosecretolytic effective amount of the compound of the formula

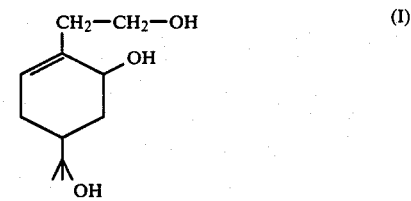

* * * * *